United States Patent [19]

Lapeyre et al.

[11] Patent Number: 4,623,350
[45] Date of Patent: Nov. 18, 1986

[54] TOTAL HEART PROTHESIS COMPRISING TWO UNCOUPLED PUMPS ASSOCIATED IN A FUNCTIONALLY UNDISSOCIABLE UNIT

[76] Inventors: Didier Lapeyre, Chaignes, 27120 Pacy sur Eure; Jean-Louis Chareire, 66, rue Aristide Briand, 92300 Levallois, both of France

[21] Appl. No.: 673,032

[22] Filed: Nov. 19, 1984

[51] Int. Cl.[4] .............................................. A61F 2/22
[52] U.S. Cl. ........................................................ 623/3
[58] Field of Search ................................................ 3/1.7

[56] References Cited

U.S. PATENT DOCUMENTS 4,240,909 12/1980 Robinson ................................. 3/1.7
4,453,537 6/1984 Spitzer ..................................... 3/1.7

Primary Examiner—Richard J. Apley
Assistant Examiner—James Prizant
Attorney, Agent, or Firm—Oblon, Fisher, Spivak, McClelland & Maier

[57] ABSTRACT

The present invention relates to a total cardiac prothesis destined to replace the sick human heart.

According to the invention, this prothesis comprises a pericardial unit (3) and an extra-pericardial unit (4), including their own electro-mechanical pumping system and interconnected through a connecting line for blood and gas (5).

The pericardial unit acts as the right heart and the extra-pericardial unit as the left heart.

20 Claims, 20 Drawing Figures

TOTAL HEART PROTHESIS COMPRISING TWO UNCOUPLED PUMPS ASSOCIATED IN A FUNCTIONALLY UNDISSOCIABLE UNITS.

The present invention concerns a total cardiac prothesis comprising two pumps, respectively representing the right heart and the left heart, as well as a control device for said pumps.

BACKGROUND OF THE INVENTION

Cardiac illness presently the first death factor in the industrial world, well before cancer. A considerable number of adults die prematurely of an unreversible heart failure, whereas their other vital functions are perfectly sane.

The causes of this plague are numerous and still obscure for the most part. Hence preventive measures cannot have a really significant effect.

Surgical techniques of bridging obstructing lesions of coronaty vessels are very efficient, since more than 400,000 sick persons are operated in the world each year. Unhappily, this surgery remains often palliative or insufficient.

Only for the United States, more than 8000 sick persons die each year during or immediately after a surgical operation on the heart; more than 100,000 sick persons, less than 65 years old, die each year of the immediate consequences of a myocardium infarct; finally, more than 50,000 sick persons, less than 65 years old die from a final invalidating cardiac insufficiency consecutive to one or several repeated infarcts.

Cardiac transplantation, i.e. the grafting on a sick receiving person of a natural heart taken from a donor, has today a renewed interest in view of the efficiency of a new specific pharmacological agent reducing the immunologic rejections pheomena. Unhappily, the shortage of available donors makes it impossible to meet the needs.

The number of applicants waiting for a cardiac transplantation increases. Many of them die prematuraly before an acceptable graft be available.

The graft of an articifial heart, mechanical alternative to the cardiac transplantation, seems accordingly to be the only solution of the future.

In order to become operative, this solution must however be of clinically acceptable form and comply with the standards of performance, confort, security and liability required by the international medical community.

More than 25 years of intensive searches and several thousands experimentations on animals in laboratories allow to consider to-day this alternative as achievable.

The history of these searches on artificial heart, the present state of the art and the prospects for the end of the nineteen eighties have been recently set forth by John T. WATSON, in charge of this field for the U.S. Federal Government, in:

"Past, Present, and Future of Mechanical Circulatory Support" J. T. WATSON, Chief, Devices and Technology Branch Division—of Heart and Vascular Diseases, National Heart, Lung, and Blood Institute NATIONAL INSTITUTES OF HEALTH, Bethesda, Md., U.S.A.

Third International Symposium on heart substitution. ROMA, ITALIE, MAY 17, 1982.

Several recent papers summarize more accurately the present situation of the practical achivements and the critical problems encountered. They are:
1. THE ARTIFICIAL HEART, William S. PIERCE Archives of Surgery, Vol. 112, December, 1977, page 1430–1438
2. CRITERIA FOR HUMAN TOTAL ARTIFICIAL HEART IMPLANTATION BASED ON STEADY STATE ANIMAL DATA. Robert K. JARVIK Trans. American Society For Artificial Internal Organs. Vol. XXIII 1977 page 533–542
3. APPROACHES TO THE ARTIFICIAL HEART, WILLIAM PIERCE Surgery, 90, 137.1981
4. THE TOTAL ARTIFICAL HEART. Robert K. JARVIK Scientificic American, 244. 74. 1981
5. THE ARTIFICIAL HEART William S. PIERCE Thoracic and cardio-vascular Surgery Editor. William W. L. GLENN, M.D. 1983. APPLETON CENTURY CROFTS
6. PRISE EN CHARGE DEFINITIVE DE LA FONCTION CARDIAQUE PAR LE COEUR ARTIFICIEL. Didier LAPEYRE. Compte-rendus des séances de la Sociétéde Biologie du Collège de France. Tome 175 N°5. 1981. p.559
7. JOURNAL OF THE INTERNATIONAL SOCIETY FOR ARTIFICIAL ORGANS. Feb. 1983. CLEVELAND Vol. 7 Number 1, Raven Press.
8. TOTAL ARTIFICIAL HEART IN TWO-STAGED CARDIAC TRANSPLANTATION Denton A. COOLEY et Al. Cardio-vascular diseases Bulletin of the Texas Heart Institute Volume 8, Number 3, September 1981

The two further following papers are of importance for the understanding of the present invention:
9. SADE, R. M., CASTANEDA A. R. THE DISPENSIBLE RIGHT VENTRICLE Surgery 77: 624–631. 1975
10. TOTAL SUPPORT OF THE CIRCULATION OF A PATIENT WITH POST-CARDIOTOMY STONE-HEART SYNDROME by a PARTIAL ARTIFICIAL HEART (ALVAD) FOR 5 DAYS . . . Lancet 1: 1125, 1978. Denton A. COOLEY et AL.

On Dec. 2, 1982 the first human application of definitive substitution to a failing natural heart of a total cardiac prothesis has been made by the surgical team of SALT. LAKE CITY (DE VRIES, JARVIK, OLSEN et Al.). This first test has been widely commented throughout the world. The first human being with an artificial heart lived 112 days with a total prothesis and an extra-body pneumatic control, conventional device commonly used on animals since more than 15 years in all the laboratories involved in this research.

In spite of a few incidents, the first utilisation on human being has proved definitely that it was possible to take over the human circulatory function by mechanical means and it has been established that the cause of the patient death was not directly linked to the cardiac prothesis. See on this subject:

THE IMPLANTATION OF THE TOTAL ARTIFICIAL HEART FOR THE TREATMENT OF END STAGE CARDIOMYOPATHY. W. C. De Vries and Al. Salt-Lake-City, Utah.

62nd Annual Meeting of the American Association for Thoracic Surgery. ATLANTA, Ga. Apr. 27, 1983.

The acquired knoledge in the state of the art, recalled in the above-mentioned papers, may be summarized in three essential observations:

(1) Since 25 years, all the experimenters which could obtain long survivals (several months) on animal, have exclusively used a pair of membrane blood pumps replacing the two ventricles of the natural heart, and an extra-body pneumatic activation. Very numerous solutions have been proposed to integrate the actuation system in the two blood pumps. However, all the devices attempting to integrate the mechanical actuation system to the blood pumps were abandonned since the weight, the excessive volume and the heat evolution are incompatible with the anatomical, physiological and biological requirements.

It has thus been necessary to uncouple the blood pumps located in the pericardium cavity from their mechanical actuation device.

However, several systems are presently developed for replacing the heavy and bulky external pneumatic console with an electro-hydraulic, electro-pneumatic of electromechanical miniaturized converter, adapted to an implantation near the blood pumps, either in the thorax or in the abdomen.

Technically more realistic solutions are those of electro-hydraulic type (see U.S. Pat. Nos. 4,173,796 and 4,369,530) or of the electro-pneumatic type.

Up to day, only one attempt of integration of the actuation means has been successful. It is that (see reference 5 above), developed by ROSENBERG and PIERCE, making use of an electromechanical converter with a pushing plate compressing blood bags of hemocompatible elastomers. A veal survived 225 days in good conditions. This is a world record of historical importance, since the animal has normally lived with a completely implanted prothesis fed externally by an electric power source. The required power was only 10 watts, whereas the weight of the animal was more than 180 kgs, i.e. twice that of a standard human dault.

However, the volume of this prothesis (900 cc) and its weight (1.1. kg) are redhibitory for human application and the miniaturizing possibilities of such an apparatus seem very limited.

The installation of machined mechanical parts in the cardiac prothesis itself, according to a configuration conforming with the shape, the volume and the weight of natural heart, appears in fact, from a technological point of view, as an insurmountable challenge.

Of course, the blood volume displaced during each cycle might be reduced to 40 or 50 cc, which would result in an important room saving. However, this reduction should obligatorily result in an increase of the operational basic frequency for maintaining an acceptable heart delivery rate. The obtained compensation would thus heavily reduce the life-time of the components.

(2) In view of the considerable difficulties encountered by the research teams at the beginning of the nineteen seventies, in order to maintain animals alive for an extended period, even when the actuation is effectued through an extra-body pneumatic console, the U.S. National Institute of Health has decided, in 1975, to devote more efforts to another alternative search way, i.e. the left ventricle assistance.

In this alternative, the ill natural heart is kept in place. An accessory artificial ventricle is parallelly branched on the circulation system and by-passes the ill left ventricle. The left ventricle is in fact the true "heart". It assumes the perfusion of all the organs under a working pressure of ten times that of the pulmonary circulation (right ventricle).

It is responsible for almost the totality of the cardiac pathology.

Conversely, it must be recalled that the right ventricle only perfuses the pulmonar tissue and that, in normal conditions, its motive function on the circulating blood is very low.

The concept of parallel operation of the ill left ventricle and of an artificial assisting ventricle is hence th the more attractive as it maintains the natural heart in place, which is a much less radical process than a complete replacement. To the mere extent of psychological and emotional aspect, the left ventricle assistance seems thus a priori as a more "pratical" solution.

In a known manner the left ventricle prothesis is placed either in the thorax or under the diaphragm, in the abdomen cavity.

It may comprise an integrated system of mechanical actuation, since the bulk limitations are much less severe in the pericardium cavity.

For yield reasons, the preferred devices are mostly of the type with a pushing plate . Five apparatuses of this type has been developed since 1977.

These apparatuses are described by FRANK D. ALTIERI in a recent paper (see reference 7 above, pages 5 to 20): "Status of Implantable Energy System to Actuate and Control Ventricular Assist Devices".

Two integrated systems which can be fed from an implanted isotopic power source or from a thermal battery are also in development: University of Washington (Modified Stirling Engine) and AEROJET system (Stirling Cycle Thermo-Compressor).

Where using an electric power source, the power is transmitted through the skin, either percutaneously by use of specific materials well tolerated by the skin (carbon derivatives, polycarbonate, polytetrafluoroethylene, etc . . . ) or transcutaneously, by high frequency magnetic induction on a primary winding implanted under the skin.

The accumulated experience, as well in laboratory as in human clinic, shows that the concept of left ventricle assistance suffers, in fact, from two major disadvantages which oblige to very seriously reconsider its potential utility in human clinic.

Besides, from a technical point of view, some critical points have not yet found an acceptable solution:

Only by itself, an accessory left pump branched in parallel on the failing natural left ventricle, cannot assume the totality of the cardiac function.

More than 150 attempts have been made on human being without conclusive results. In a few cases, of short duration, the left ventricle by-pass has allowed a few sick persons having an acute insufficiency of left ventricle to pass a difficult cape, immediately following a surgical operation of the heart.

These cases are unhappily very scarce. Although the U.S. National Institute of Health has autorized application to human being, in various cardiology centers, since 1979, the method was not conclusive for the users. Some of its promoters, such as DENTON A. COOLEY, have even given up.

For sick persons with an invalidating left ventricle chronic insufficiency (theoretically the best indication for ventricle assistance), the cardiologists and heart surgeons are higly reluctant to use a heavy method which may hasten the fatal termination and which, in every case, is conditioned by the aleatory possible failure of the right ventricle function.

Moreover, it is considered that the relief of the sick left ventricle by the auxiliary artificial ventricle would favor the progressive decrease of the right ventricle performances. (see: EFFETCS OF LEFT HEART BY-PASS ON RIGHT VENTRICULAR FUNCTIONS, A. T. MIYAMOTO et Al. Vol. XXVIII TRANS AM. SOC. ARTIF. INTERN ORGANS 1983, page 543).

Finally, two critical technical points yet remain unsolved:

1. The placing of a membrane either in the tip of the sick left ventricle or upstream thereto in the left auricle, results in phenomena of mechanical impediment to the feeding of the accessory ventricle (plicatures, bendings, pressure drops, resulting from an insufficient section, coagulation . . . ).

2. The rate of delivery of the auxiliary left ventricle must be controlled by the feeding pressure of the natural left ventricle, itself function of the delivery of the right ventricle. In the case where the venous return delivery decreases, for example at rest, the blood by pass rate through the auxiliary ventricle may be very low, thus producing in the feeding duct of the auxiliary ventricle the formation of a cellular proliferation ("pannus") which tends to progressively obstruct it, since this phenomenon, once begun, self-develops for obvious hydraulic reasons.

To resume, the experience of these twenty-five last years, as well in the field of total heart replacement as in that of left ventricular assistance, gives the following informations, well-known in the art:

(1) It is to-day technically impossible to connect, in the pericardium cavity of a human being, in lieu of the failing natural heart, a total cardiac prothesis and its mechanical actuation system, in view of the fact that the natural heart of a man has, as an average, a weight from 300 to 350 g and that of a woman 250 to 300 g, and, when the heart is full with blood (diastole), its volume does not exceed 550 cc.

Of course, numerous cardiac sick persons suffer from a substantial increase of the heart volume ("cardiomegaly").

Unhappily, the very large majority of applicants for a total cardiac replacement by artificial heart pertain to the category of ischiema cardiomyopathes with coronaty lesions. These sick persons do not suffer from a significant increase of the heart volume.

A total cardiac prothesis must not have a weight and a volume substantially greater than the weight and the volume of the natural heart. Bulk linitations are not only of physical order (available volume); they have, in fact, operational critical effects, as shown hereinafter. It is thus necessary to anatomically uncouple the intra-pericardial blood pumps from the mechanical devices actuating said pumps.

(2) Several thousands of experimentations on animal, and a few ones on human being, have shown that it was possible to place, externally to the pericardium cavity, either in the thorax or in the abdomen cavity, or in retro-peritoneal position a pump and its actuation means. Such spaces are considered as "physiologically neutral" and they can easily receive mechanical systems of a volume larger than 900 cc, for a weight which may reach, without inconvenience, 1000 to 12000 grams.

(3) The U.S. Pat. Nos. 4,173,796, 4,222,127 and 4,369,530, recall, in a general and non exhaustive manner, the main technical objects to achive when making a standardized total cardiac prothesis able to efficiently replace a failing human natural heart, in an acceptable technical form.

It will be observed that some of these objects are not yet achieved and constitute critical points well known in the art.

These critical points must however be classified according to a fundamental priority order, since the solution of some of them depends on solutions which can be found for others. This hierarchy of priorities must be expressed clearly.

First of all, anatomic requirements must be complied with, since they have a critical incidence on the prothesis function. A cardiac prothesis must obviously reproduce the pumping capacity, if not of an athlete natural jeart, at least of a heart graft taken from a donor. Th functional capacities must allow a sick person with a transplanted heart to move, to make current exercises such as walk, or even swimming. Studies on sick persons having undergone a cardiac transplantation have shown that the capacities ("pumping capacities") of a prothesis should range between the limit values of 3 and 10 l. per minute.

Although the delivery rate varies in accordance with the metabolic demands within the above-mentioned limits, it should be observed that the average delivery rate for a standard adult is about 4 liters per minute during more than 95% of the time. Finally, the frequency varies only to a small extent and remains close to 70 cycles per minute, with a distribution in the cycle of the order of 35% for the systole and 65% for the filling time, the frequency variations being essentially the result of a variation in the filling time whereas the systole time remains substantially constant (with 5% of variation).

Another fundamental point to be recalled, closely related to the first one, is an elementary physiological notion, universal by admitted to-day, but which was yet controversial during the last ten years. The heart is a response-organ, whose funtional capacities must assume variations in the feeding rate, which variations are themselves related to variations of the metabolic activity of the organism. In other terms, the cardiac pump is the slave and the organism is the master. This fundamental principle makes necessary a control of the delivery rate based on the variations of the return flow rate, the pilot signal being the return blood pressure, since an increase of metabolic demands of the organism results in a decrease in the resistance of the circuit, producing an increase of the return flow rate. The natural cardiac pump reacts with a very high sensitivity, by variations in the frequency of the pulsed volume and in the contraction force, to variations of the feeding pressure and to the variations of the output resistance. This sensitivity has been measured. It is about of one liter per minute and per mercury millimeter of pressure. Thus, practically, an artificial heart must react to an increase of the feeding pressure of the right heart of about 10 millimeters of mercury by a variation of the delivery rate from 3 to 10 liters per minute within a relatively short response time, not exceeding a few seconds.

A third fundamental point is still of physiological order. The cardiac pump is fed through two veins of large diameter, i.e. vena cava superior and vena cava inferior, opening in a feeding reservoir formed by the right auricle. Similarly, the left ventricle is fed throught four pulmonary veins, i.e.; the right superior and inferior pulmonary veins and the left superior pulmonary veins, opening in the feeding reservoir formed by the left auricle. These veins and feeding reservoirs are very flexible and hence can be easily compressed when the bulk of the cardiac prothesis is excessive. These veins or ducts without radial rigidity are hence radially collapsable, which forbids any aspiration or active depression to; facilitate the filling. These particular filling structures are thus an essential critical point which is the more important as the ratio pressure/volume (compliance) of the upstream venous network is very low. A small increase in the resistances to filling of the cardiac pump thus results in a pressure increase in the network, which produces a very substantial increase in the volume of the venous circuit. A substantial part of the circulating volume may thus be kept in reserve or retained in the venous circuit, thus decreasing to the same extent the input flow to the blood pump.

The problem of adapting the shape, the volume and the weight of the cardiac prothesis to the free space made available in the pericardium cavity by ablation of the sick natural heart is not only a problem of physics, geometry and volume. The limitations as to the shape, the volume and the weight have, in addition, for the above-explained reasons, a direct determinent effect on the return flow rate, and hence on the functional characteristics of the cardiac pump.

By successive approaches and multiple slight adaptations, it has been possible, after several thousands of experimentations on animal, to solve in an acceptable manner this problem of adaptation in shape, volume and xeight on animal, which explains the extended survival today currently obtained in laboratory.

However, the anatomical limitations of human being are radically different from those of the animal and the results obtained by experimentation on animals cannot, in this field, be transposed to the human being. It is clear, in pratice for the cardiac surgeon, that the geometry of the cardiac prothesis must before all coincide into the configuration of the space left available by the ablation of the sick natural heart. On the contrary it is not acceptable that the thorax cavity of the sick person will have to conform to the geometry of the prothesis. Now, the applicants for receiving the cardiac prothesis are selected from those who have a pericardium cavity as large as possible in ordre to be able to house a bulky prothesis.

It must be further observed that this bulky prothesis cannot be directly coupled in the pericardium with a mechanical actuation system. As a matter of fact, such mechanical actuation systems will still increase the volume of the prothesis. It is hence necessary to provide the prothesis, but outside the pericardium, with electropneumatic of electro-hydraulic converters. But then the total yield of such prothesis is relatively low and a source of relatively high power (about 10 to 15 Watts) must be necessary.

In the present state of the art, in the field of the most performing electric generators, a 10 Watts power cannot be provided but by a battery of a weight higher than 1 kg, in order to obtain a complete autonomy of more than 3 hours with a portable battery. This results in constraints which are, for the patient, a factor of uncomfort. Moreover, the relatively low yield of the electro-pneumatic and electro-hydraulic converters results in a heat evolution liable to generate hot points in the converter.

In addition to the anatomical and psychological limitations, mentioned above, while taking into account the geometry, the weight and the volume of the artificial blood pump which must replace the failing natural heart, other standards must obligatorily be complied with in order that the artificial heart become effectively acceptable in human clinic. These standards are much, better explained in the state of the art than the anatomical and psychological limitations which, nevertheless, are prioritary.

These standards are of three orders, i.e.: biological, technological and economical (the cost of a prothesis must be as low as possible).

The biological standards concern the use of specific materials for the parts of the blood pumps which are in contact with the blood stream. These materials must be neutral vis-á-vis to the natural biological phenomena which condition the blood coagulation, when blood is in contact with an extraneous surface; These materials must, in addition, be non-toxic and must not generate local inflammatory reactions. Presently, a certain number of flexible plastic materials are used successfully for making membrane pumps.

FIELD OF THE INVENTION

The experience has shown that this type of pumps was that giving the best results. However, after several months of use on the animal, calcifications may occur at the level of the membranes, at the locations thereof which undergo the maximum mechanical stresses at each pumping cycle. Thus, an important factor of long life of these materials in contact with blood consists in the limitation of the mechanical stresses and it is one of the objects of the present invention. To provide a membrane pump in which the membrane is subject to very low mechanical stresses.

The technological standards known in the art define the threshold of quality which must be achieved in order to obtain an artificial heart able to be used currently in the everyday therapeutic case of surgical instruments of the cardiac surgeon. They concern liability, security, performances and comfort. As far as comfort is concerned, the prothesis must have a very low acoustic level, no vibration or gyroscopic phenomenon. Moreover, the maintenance must be simple and a sufficient miniaturization must be achievable.

In the technological standards, the yield of the system is presently the determinant critical point. As a matter of fact, in view of the pression drops at the level of the blood pump, essentially occurring in valvular devices, in view of the thermo-dynamic losses occurring in the converter and of the yield of the electric conversion in transcutaneous transmission, the global yield must be optimized so as to reduce to a minimum the power amount to be supplied.

As a matter of fact, in order that the sick persons may have a sufficient autonomy and freedom of movement, this power must be supplied, at least temporarily, by means of a portable battery.

It is obvious that the higher is the yield, the lower is the power to be supplied and the longer is the operation autonomy of the system for a given weight of accumulator. The prothesis according to the invention is adapted to be fed with a power about 5 to 7 watts for a standard adult at rest.

Generally, the object of tje invention is, in view of the experience of the last 20 years of research on artificial heart, the achievement of a total cardiac pulp able to comply with the anatomical and physiological priorities and the biological, technological and economical standards listed above.

The most important pecullarity of the present invention resides in the solution of the critical problem of the bulk of the blood pumps to be located in the pericardium in place of the sick heart, since this solution offers determinant advantages in the operation of the prothesis and optimizes the reproduction of the performances or a natural sane heart.

SUMMARY OF THE INVENTION

For this purpose, according to the invention, the total cardiac prothesis comprises two pumps, respectively representating the right heart and the left heart, as well as a device for controlling said pumps. It is remarkable in that prothesis also said control devies actuate said pumps in opposition, and said comprises an undissociable functional unit formed by:

a pericardial unit, adapted to be housed in the cavity of the normal heart to be replaced and enclosed in a tight envelope comprising four coupling orifices respectively destined to be connected to the right auricle, to the pulmonary artery, to the left auricle and to the aorta, said orifices for coupling the right auricle to the pulmonary artery being provided with valves respectively used as inlet orifice and outlet orifice of a first pump housed in said pericardial unit and destined to assume the right heart function of the natural heart to be replaced;

An extra-pericardial unit, destined to be housed in a physiologically neutral space of the receiving sick person and to assume the function of the left heart of the natural heart to be replaced, this extra-pericardial unit comprising a tight envelope wherein is enclosed a second pump provided with an inlet orifice andan outlet orifice, each provided with a valve;

A multi-functional connection between the pericardial and extra pericardial units, comprising:

A first duct passing through the envelope of the pericardial unit and connecting the orifice of the latter corresponding to the left auricle with the inlet orifice of said second pump housed in said extra-pericardial unit;

A second duct passing through the envelope of said pericardial unit and connecting the orifice thereof corresponding, to aorta with the outlet orifice of said second pump, housed in said extra-pericardial unit;

A third duct establishing communication for gases between the sides of said first and second pump opposite to the blood flow passing therethrought;

Thus, thanks to said dispersed structure, although in an undissociable single block, of the prothesis according to the invention, only the pericardial unit, i.e. the right heart, is housed in the pericardial cavity.

Accordingly, the required room is available for housing an envelope containing the pump and its electromechanical actuation system, acting as right ventricle.

Thus, according to an important feature of the present invention, said pericardial unit comprises an electromechanical system for actuating said first pump.

As a matter of fact and already pentioned, the right heart does not provide but a very low blood pressure difference, so that it requires only a small power. This observation associated to the gain of room in the pericardial cavity due to the remote location of the left heart, makes it possible to house in said pericardial unit an electro-mechanical system for directly actuating said first pump, i.e. a high yield system. Consequently, the total power required for the operation of the prothesis according to the invention is reduced. Moreover, the conversion of electric power to mechanical power is obtained with a good yield in said electro-mechanical system, only few heat evolving during this conversion, so that the thermal balance of the sick person is,not disturbed and the liability of apparition of hot points on the envelope of the pericardial unit is non-existent.

Preferably, said connection joins the lower part of the envelope of said pericardial unit to the upper part of the envelope of said extra-pericardial unit.

Advantageously, the envelope of said pericardial unit has, at least approximately, the shape, the volume and the weight of the sick natural heart to be replaced and, in said envelope, the position of the orifices for connection to the right auricle, to the pulmonary artery, to the left auricle and to aorta correspond at least substantially to the natural position of said auricles and arteries. As a matter of fact, the room released in the pericardial cavity by the remote location of the pump, acting as left heart, makes it possible to arrange said pericardial unit so that the connection to the veins and arteries be as optimum as possible. In these conditions, the prothesis according to the invention cannot disturb at all the venous blood return through the venal cave and pulmonary veins, and it is then possible to adjust the pulsation frequency of the prothesis in response to the blood return pressure in the right heart, which is particularly advantageous. As a matter of fact, the right heart is more sensitive for the regulation of the blood flow rate, since it receives non-oxygenated blood returning from the organism ("the Master") before feeding it to the lungs. It is thus of particular interest to maintain the right heart in the pericardial cavity.

Consequently, according to another feature of the present invention, a sensor is placed in the pericardial unit to detect the venous blood pressure at the input of said first pump and to regulate the operation of the total prothesis in response to the measured pressure.

In addition, the remote location of the left heart frome the pericardial cavity may provide sufficient room to house in said pericardial unit the control mechanisms of the electric-control valves.

It is thus advantageous, particularly with respect to the yield, that the valves provided in the orifices for connection to the right auricle and to the pulmonary artery be electric-control valves. As a matter of fact, everything else being unchanged in the hydraulic qualities of the valves, the capacity of controlling their movement increases the total pumping yield, particularly by preventing leaks at the closure.

Preferably, said first pump is of the membrane type and said electro-mechanical system is then of the type with a pushing-plate in direct contact with said membrane. The biological quality of the prothesis according to the invention can hence be also optimized by, so conforming-said plate that it results in the minimum formation of microcracks in the membrane, these microcracks being, as it is well known, a factor of degradation of the quality of the motive membrane of the prothesis.

The above mentioned sensor, destined to regulate the operation of the prothesis, may then be mounted on the membrane of said first pump.

It should be observed, in addition, that by using, without any inconvenience as already mentioned, a physiologically neutral space, for exemple thorax or abdomen to house said extrapericardial unit, the invention provides a considerable advantage. As a matter of fact, said physiologically neutral psace may be selected of easy access by means of a minor surgical operation, so that said extra-pericardial unit, which is the power unit and hence the more subject to wear, in case of failure will be, easily replaced with a new unit of faultless operation.

In order to facilitate such an exchange, it is advantageous that the envelope of said extra-pericardial unit comprises orifices for respective connection to the inlet orifice, the outlet orifice and the side of said second pump opposite to the blood and adapted to be easily connected to or disconnected from said first, second and third ducts of said connection between the units.

Since the volume of the selected physiologically neutral space may be relatively substantial (up to 1 liter), no bulk problem arises and said extra-pericardialial unit may also incorporate an electro-mechanical system of high yield for directly actuating said second pump. The latter may also be of the membrane type, so that the associated electro-mechanical system is then of the type having a pushing-plate in direct contact with said membrane.

Preferably, each of the two valves incorporated in said extra-pericardial unit is of the type with controlled opening and closure, as those provided in said pericardial unit. It is then adventageous to provide the prothesis control device with a micro-processor controlling the electro-mechanical systems incorporated in said units, as well as the four valves thereof. This micro-processor then receives form the sensor placed in the pericardial unit the informations which make possible the adjustment of the cardiac rythm to the needs of the sick person.

According to an essential feature of the present invention, said third duct of said connection between the pericardial and extra-pericardial units is longitudinally flexible, but radially rigid, and it contains the first and second ducts Thus, said first and second ducts are mechanically protected by the third one. This is particularly advantageous since, as stated hereinafter, said first duct may be very flexible and hence very thin and is not be subjected to any induced, pressure drop. The second duct may be more rigid and thicker. It results that the arrangement according to the invention provides for the protection of the first duct, which is fragile, by the two other ducts. As also stated hereinafter, said first duct, associated to the internal space of said third duct, also acts as complementary left auricle. It will be observed that, thanks to said third duct, said connection between the units acts as "compliance chamber" (chamber for compression of the gas volume and valancing chamber) for the whole prothesis.

An electrical cable connecting said pericardial and extra-pericardial units may be passed through said third duct. Thus, the control of the electro-mechanical system and of the valves of said pericardial unit may pass through the extra-pericardial unit and the electric cable contained in the connection line.

Each electro-mechanical system may comprise an electric motor and a rod-crank system avoiding the reversion of the revolving direction of said electric motor. Moreover the relative location of the articulations of the pushing-plate, of the rod and the crank may be advantageously so determined that the forward and backward velocities of the said pushing-plate be adapted to the physiological requirements and necessitate only a slight cyclic adaptation of the motor running speed.

Preferably, when the pericardial unit is of elongate shape, the pushing-plate is articulated about one axis whose general direction is at least substantially parallel to the lenght of said unit so that the surface of said pushing-plate be as large as possible.

Said electric-control valves may be of the type with a circular clapper revolving about one of its diameter or sliding along its plane. They may also be each formed of two semi-circular clappers articulated about a common diameter and which may take every position between a first external position at which they are coplanar and opposite and a second external position at which they are joined back to back.

The figures of the accompanying drawings will make easier the understanding of the invention. On these figures, identical references designate similar elements.

Figures 1, 2, 3:
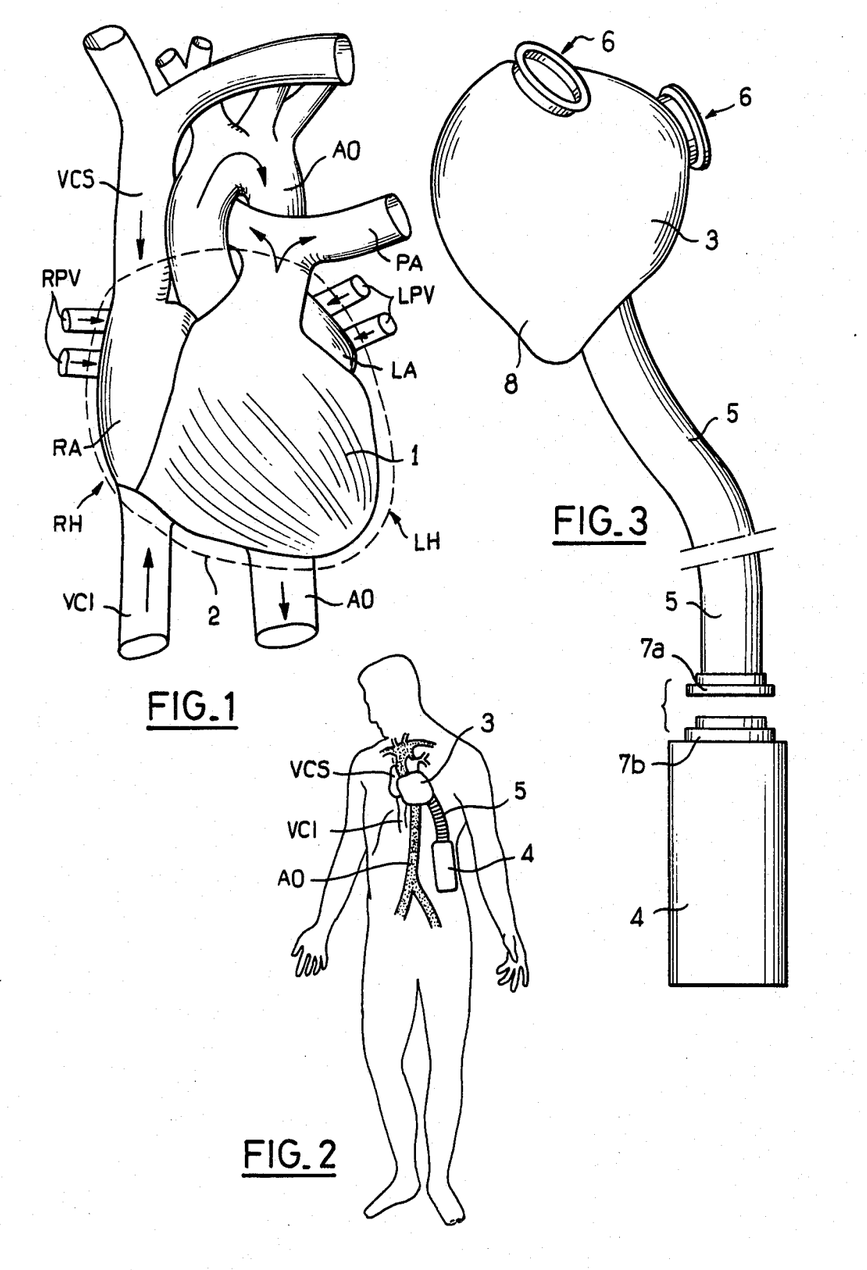
FIG. 1 diagrammatically shows a natural heart in connection with its main veins and arteries, as a front view.
FIG. 2 diagrammatically illustrates the principle of the present invention.
FIG. 3 diagrammatically shows an external view of an embodiment of the total cardiac prothesis according to the invention.

As shown in FIG. 1, a natural human heart 1 is housed in the pericardial cavity 2 (merely shown by dash-line 2) and is formed in fact of two distinct hearts, however integral with each other, i.e. the right heart RH comprising the right auricle RA and the right ventricle and the left heart LH comprising the left auricle RA and the left ventricle. The right auricle LA of the right heart RH receives venous blood through vena cava superior VCS and through vena cava inferior VCI, whereas the ventricle of said right heart RH transfers the so-received blood to the lungs through the pulmonary artery PA.

Similarly, the auricle LA of the left heart RH receives the blood from the lungs through the left pulmonary vein LPV and the right pulmonary vein RPV and the ventricle of the left heart LH expells the received blood through aorta AO.

The basic idea of the present invention lies in the physiological observation, above recalled, that, although it is formed by two pumps RH and LH, forming a single muscular unit, the heart 1 is in fact composed of two functionally independent assemblies. As a matter of fact, functionally, the right heart RH may be considered as a mere heart of passage which expels a blood column whose flowing velocity is variable but never nil except when the heart pulsations are very low. When the blood rate of the vascular system increases as a result of an increased frequency of these pulsations, the participation of the right heart RH to the circulation of blood in the pulmonary circuit decreases as a result of the speed increase, and hence of the cinetic energy of the blood reaching the right heart RH.

On the contrary, the left heart LH constitutes the proper heart, i.e. the propulsive pump having the charge of assuming the blood perfusion of all the organs and tissues of the organism.

Moreover, the fundamental idea of the invention is based on the fact, known in the Art, that the contraction of the right heart ventricle and that of the left heart ventricle cannot be simultaneous but in phase opposition.

As diagrammatically illustrated in FIG. 2, the total cardiac prothesis according to the invention comprises a functionally undissociable unit formed of two uncoupled pump units 3 and 4 connected to each other through a functional tubular connection line 5.

The pumping unit 3, destined to replace the right heart RH of the natural heart 1 is housed in the pericardium cavity 2. It comprises four coupling ends of any known type, not shown, respectively destined to couple the right auricle RA (venae cava VCI and VCS), to the pulmonary artery PA, to the left auricle LA (left and right pulmonar veins LPV and RPV), and to aorta AO, after cut of the latter and exerisis of the natural ventricles 1 from the pericardium cavity 2.

The pumping unit 4, destined to replace the left ventricle of the natural heart 1, is housed outside the pericardium cavity 2, in a physiologically neutral space, for example thorax or abdomen.

The connection line 5, which may without disadvantage pass through the diaphragm, comprises three ducts, two of which respectively connect the pumping unit 4 to the coupling ends of the pumping unit 3, themselves respectively connected to the left auricle LA and to aorta AO.

Advantageous embodiments of the two pumping units 3 and 4 and of the connection line 5 are hereinafter described more in detail. However, the following remarks can be made concerning the total cardiac prothesis 3, 4, 5 of the invention, as illustrated in FIG. 2:

(1) the bulk saving obtained by removal of the left ventricle from the pericardium cavity, makes possible:

(a) to house, inside unit 3, pumping means, preferably of the type with a flexible membrane and a pushing plate, and their actuation means;

(b) optionally, to associate to the ends of the coupling to the right auricle RA and to the pulmonary artery PA, electric-control valves, more advantageous but more bulky that the simple valves usually mounted in the ends of the presently known cardiac protheses;

(c) to optimize the prothesis valvular system, i.e. the location of the ends of the coupling to auricles and arteries. These coupling ends, or at least some of them, may have a position identical to that of the natural orifices, so that the prothesis does not disturb at all the venous blood return. Consequently, it is possible without difficulty to adjust the pulsation frequency of the prothesis in response to the blood return pressure at the pumping unit 3, simulating the right heart RH.

(2) The pericardial pumping unit 3, forming the prothesis of the right heart RH, effects the same work as the latter, i.e., most often, a mere accompanying or contribution work to the blood passage. The pumping unit 3 is hence subject to only few strains and to a few wears, so that its operation may be satisfactory over many years. Accordingly, there is no counter-indication to house this unit in the pericardium cavity 2, whose access through the thorax requires a surgical operation which is delicate and important for the surgeon and exhausting for the sick person. The pumping unit 3 will then except for particular exceptional cases, be implanted definitely or at least for a long time in the pericardium cavity 2.

(3) The extra-pericardial pumping unit 4, simulating the left heart, makes a substantial work and is the more subject to straining and hence the more liable to require a replacement. It is hence advantageous to locate it in a physiologically neutral space, such as abdomen, of easy access through a gentle surgical operation. Moreover, this unit 4 being located in a space where the bulk limitations are still clearly critical, it may incorporate its own pumping means, preferable of the type with a flexible membrane and a pushing plate and their actuation means and it may comprise electric-control valves.

The above remarks 2 and 3 make apparent, on the one hand, that there is no disadvantage in the mounting of the pericardial pumping unit 3 and of the connection line 5 as a monolithic block and, on the other hand, that it is advantageous to provide a quick connection system for coupling the extra-pericardial pumping unit 4 with the connection line 5. This structure is represented in FIG. 3, showing the pericardial unit 3, provided with quick connection ends 6 (only two of which are apparent) for connecting it to the auricles RA and LA, the pulmonary artery PA and aorta AO, is rigidly seamed to the connecting line 5, whereas the latter may be connected to the extra-pericardial pumping unit 4, through the quick connection system 7a, 7b. This connection line 5 connects the lower part of the pericardial unit 3 to the upper part of the extra-pericardial unit 4.

Figures 4, 5:
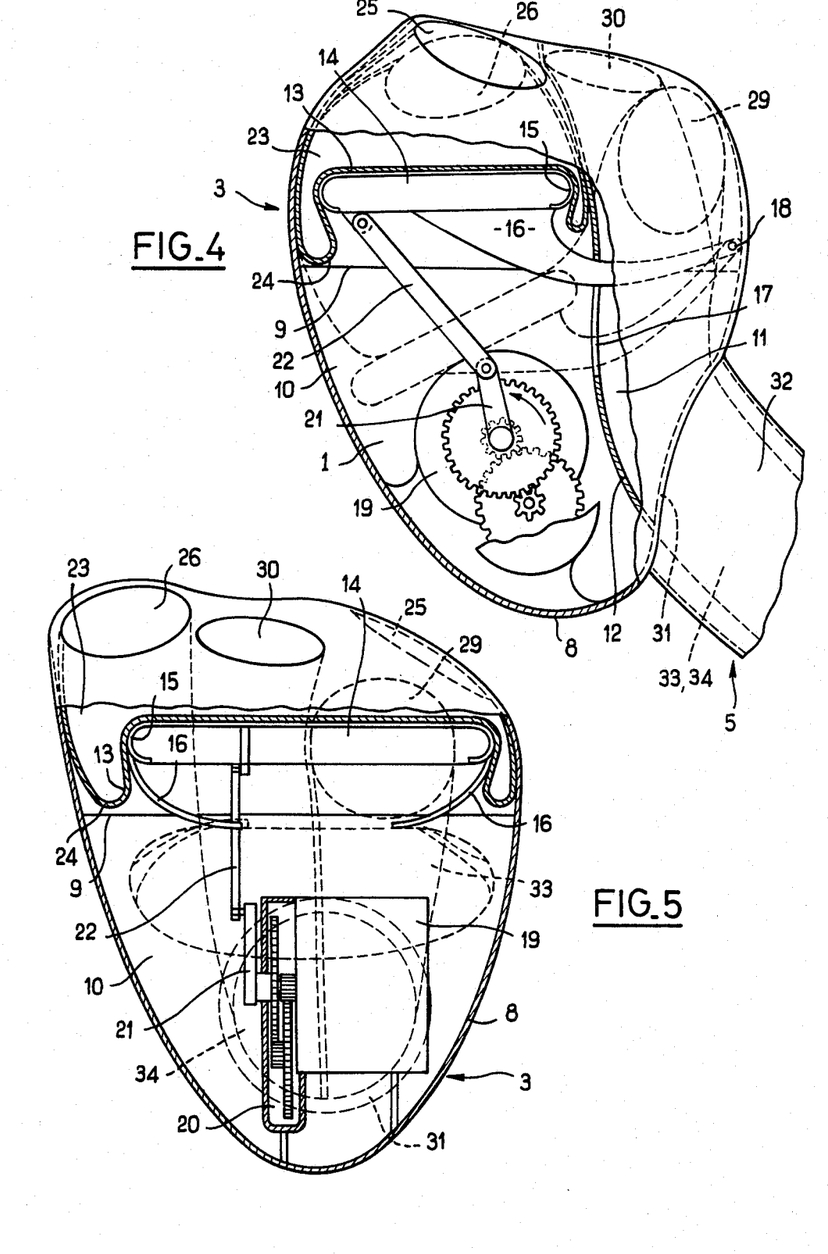
FIGS. 4, 5 and 6 show an exemple of embodiment of a pericardial unit for the cardiac prothesis according to the invention, respectively in front view, in left view and in view from above with torn-out parts.
Figures 6, 7:
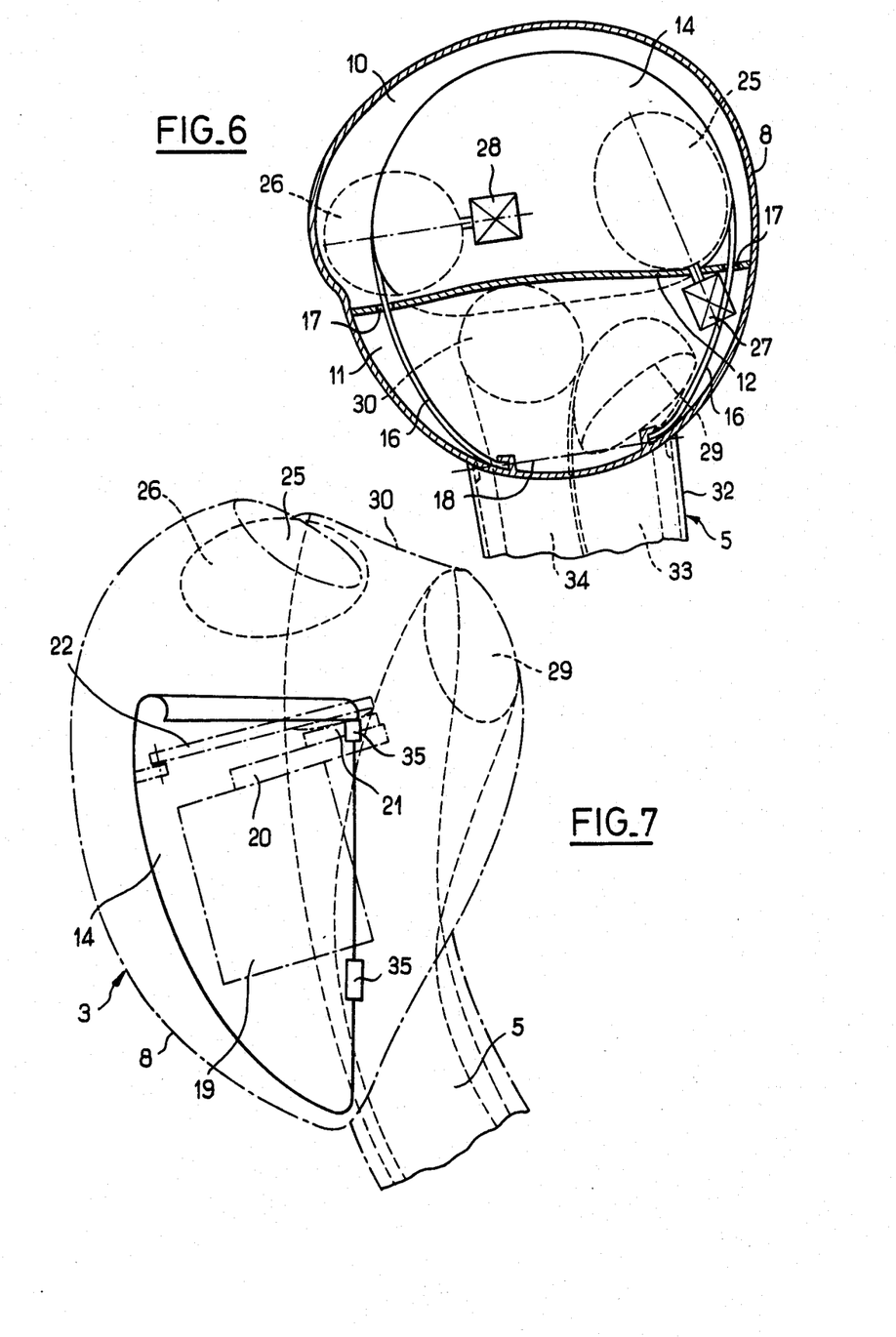
FIGS. 7, 8 and 9 are shematic views, respectively comparable to those of FIGS. 4, 5 and 6, illustrating an alternative embodiment of arrangement of the pushing-plate of the membrane pump for the pericardial unit.

The embodiment of pericardial pumping unit 3, shown in FIGS. 4, 5 and 6, is provided with an external envelope 8. It is formed for example of two parts assembled along the joining plane 9. The envelope 8 has at least approximately the shape of a natural heart.

The internal volume of the envelope 8 is divided in two cavities 10 and 11, by a longitudinal partition 12. In the greater cavity, i.e. cavity 10, is arranged a pump, provided with a membrane 13 of hemocompatible material, such as a polyurethane, and with a pushing plate 14, whose peripheral edge 15 is rounded and spaced apart from the internal wall of cavity 10.

The pushing plate 14 is provided with arms 16, oriented generally in a direction substantially parallel to the plane of said pushing plate. Arms 16 cross the wall 12 through slots 17 and are articulated, at their ends opposite to the pushing plate 14, about an axis 18 parallel to the plane of the latter and arranged in the internal wall of the envelope 8, in cavity 11.

It must be observed that the slots 17 provide, in addition to a passage way for arms 16, communication means for gases between cavities 10 and 11.

The pushing plate 14 is actuated by an electric motor 19, through a reducer 20, in a lubricated tight casing, and a crank 21 associated to a rod 22.

Membrane 13 is kept in place by the internal wall of envelope 8 and wall 12 and defines, inside cavity 10, a tight hemocompatible bag 23, wherethrough the blood passes. In order to avoid as much as possible the mechanical strains imparted to membrane 13 by the pushing plate 14, the latter is simply laid on said plate, while forming a peripheral gutter around the latter, said gutter 24 being located between the rounded edge 15 of the pushing plate 14 and the internal wall of cavity 10. Thus, during the motion of pump 13, 14, the gutter 24 forms a membrane reserve which may roll with respect to said pushing plate 14, thereby substantially reducing the strains.

The tight bag 23 comprises a blood inlet orifice 25 and a blood outlet orifice 26, respectively destined to be connected to the right auricle RA and the pulmonary artery RA. The orifices 25 and 26 are, for this purpose, provided each with a quick coupling end 6 which may be of any known type and which is not shown on FIGS. 4 to 6 for seek of clarity. These quick coupling ends are provided with electric-control valves.

FIG. 6 diagrammatically shows the control electromagnets 27 and 28 of said valves. In this figure, the diagrammatically shown valves are of the type with a clapper which may oscillate about a diameter, by action of said electro-magnets.

Electric-control valves which can be used in the prothesis of the invention will be described hereinafter more in detail. However, it should be observed that this type of valve is not limitative, since the axis of the clapper may be positioned at another place or the valves may be, for example, built in several parts.

Thus, by action of motor 19, pushing plate 14 and membrane 13, alternatively pass from the extreme position of blood output (shown in solid line in FIGS. 4 and 5) to the extreme position of blood input (shown in dotted line in FIGS. 4 and 5).

The speed of motor 19 (and hence the rythm of pump 13, 14) as well as the opening and closing of the valves placed in orifices 25 and 26, are at every moment determined by a micro-processor (not shown) receiving informations from a sensor, also not shown for sake of clarity of the drawing, placed against membrane 13.

It will be observed that the system of rod 22 and crank 21, although being replacable by any other appropriate mechanical device, offers the following substantial advantages:

it makes possible to avoid the reversion of the revolving direction of the motor 19 at each filling and emptying of bag 23;

it makes possible, thanks to the respective locations of the pushing plate 14, of axis 18 and motor 19, to obtain substantial velocity differences for the upward and downward stroke of the pushing plate 14, in response to small cyclic speed variations of motor 19. It is thus possible to approximate the physiological conditions of pumping, wherein the diastole time is very different from the systole time.

Cavity 11 of envelope 8 is provided with orifices 29, 30 and 31, across the wall of the latter. Orifices 29 and 30 are each provided with a quick coupling device 6 (not shown in FIGS. 4 to 6) and are respectively destined to be connected to the left auricle LA and to aorta AO.

Orifice 31 is provided for establishing communication between cavity 11 and the tubular envelope 32 of the connection line 5.

Moreover, pipes 33 and 34, tightly connected to the coupling ends 6 of orifices 29 and 30 respectively, pass through cavity 11 and in the tubular envelope 32 of the connection line 5, through orifice 31, in the direction of the extra-pericardial pumping unit 4.

Thus, pipe 33 extends the left auricle and transfers blood from the lung to the extra-pericardial unit 4. On the contrary, pipe 34 expels blood from the extra-pericardial unit 4 to aorta AO. Pipe 33 is made of hemocompatible material; however, as stated hereinafter, it is advantageous that pipe 33 be only of low rigidity so that it can complete the action of the left auricle LA, whereas pipe 34 is unextensible.

The location of orifices 25, 26, 29 and 30 conforms with the natural disposition, but only orifices 25 and 26 are provided with valves.

It will be observed that thanks to the slots 17 of wall 12, the inner space 36 of envelope 32 of connection line 5 (see FIG. 10) is in connection with the dead space formed by the part of cavity 10 which is external to bag 23, and wherein is housed the pumping mechanism 14, 19, 20, 21, 22.

In the embodiment of FIGS. 4 to 6, the axis of motor 19 is substantially transversal to the larger dimension of envelope 8, whereas the displacement of the pushing plate 14 is substantially parallel to said larger dimension. On the contrary, in the alternative embodiment of FIGS. 7, 8 and 9, the pushing plate displacement is substantially transversal to the larger dimension of envelope 8. The pushing plate 14, instead of being plane, is curved and is actuated by motor 19, whose axis is substantially parallel to said larger dimension (motor 19, reducer 20, crank 21 and rod 22 are indicated only in FIG. 7). The pushing plate is articulated by means of hinges 35, allowing a deflection in the direction of arrow F in FIG. 9.

Figures 8, 10:
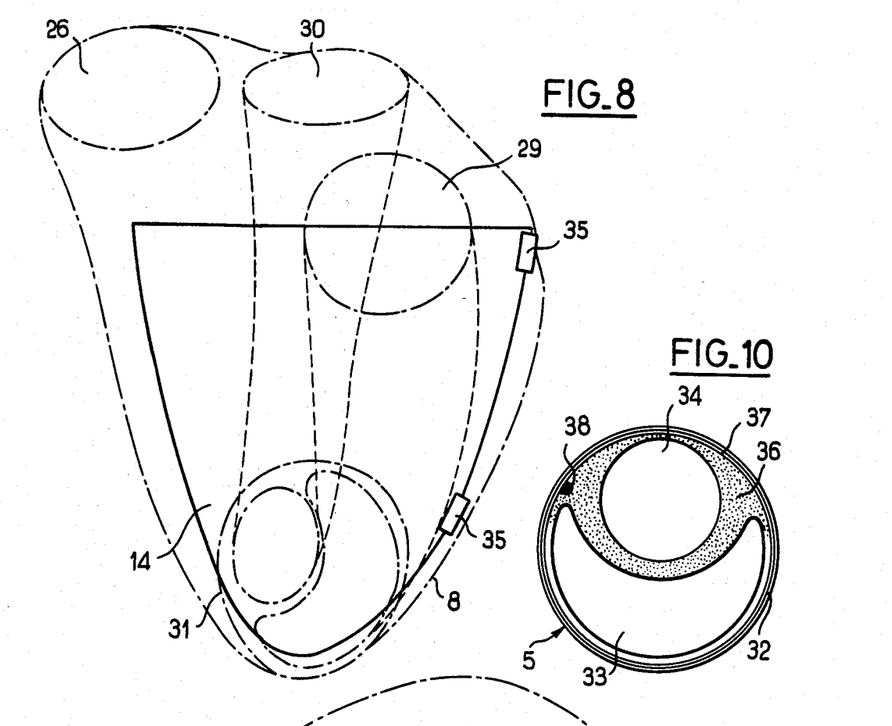
FIG. 10 is a transversal cross-section of the tubular connection between the two prothesis units according to the invention.
Figure 9:
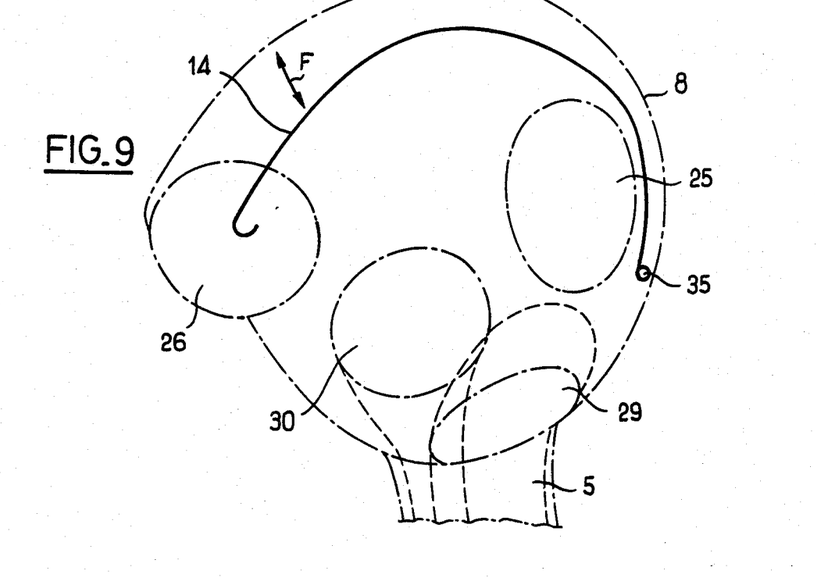

The embodiment of FIGS. 7 to 9 is particularly advantageous, since it makes possible to use a pushing plate 14 of large surface; hence it becomes to reduce the amplitude of displacement of the pushing plate 14 (for an identical pumping capacity) and accordingly to reduce the strains applied to membrane 13. The latter will consequently have a longer life time.

FIG. 10 shows, in transversal cross-section, an advantageous embodiment of the tubular connection line 5. As shown, the flexible pipe 33 has a crescent-shaped section for adaptation between envelope 32 and the more rigid pipe 34.

Envelope 32 has a sufficient longitudinal flexibility for being the best as possible adapted to the physiological passage-way which may exist between the pericardial cavity 2, wherein is located the pumping unit 3, and the extra-pericardial cavity, wherein is located the pumping unit 4. On the contrary, the envelope 32 is of high radial rigidity, in order to avoid any formation of folds.

This envelope 32 may, for example, comprise in its wall for this purpose a helical or substantially helical wire 37. The diameter of the tubular envelope 32 may be of about 5 cm.

Inside said envelope 32, as abovementioned, is housed a flexible pipe 33 extending the left auricle in a common pulmonary vein, wherein the left and right pulmonary veins open, the more rigid pipe 34 extending the aorta, and an electric connection 38 connecting the pumping unit 3 to the pumping unit 4 and to an electric generator. The electric connection 38 is also used for feeding and controlling motor 19 and electro-magnets 27 and 28 of the electric-control valves located in orifices 25 and 26.

In order to reduce the pressure dorps, the flexible pipe 33 may be of a section larger than 8 cm$^2$, whereas the section of the rigid pipe (aorta) must be greater than 4 cm$^2$.

Pipes 33 and 34 and the electric connection 38 leave, inside tubular envelope 32, a free space 36 establishing communication for gases between the dead spaces of the two pumping units 3 and 4.

The following remarks can be made concerning the structure of the connection line 5:

(1) In order to be adapted to the left auricle and to the pulmonary veins, pipe 33 must be very flexible and have a consistency close to that of the gold-beater's skin. Pipe 33 is hence very fragile. However, this is not a disadvantage since, in the connection line 5, pipe 33 is well protected between tubes 32 and 34, which are more rigid.

Figures 11, 13:
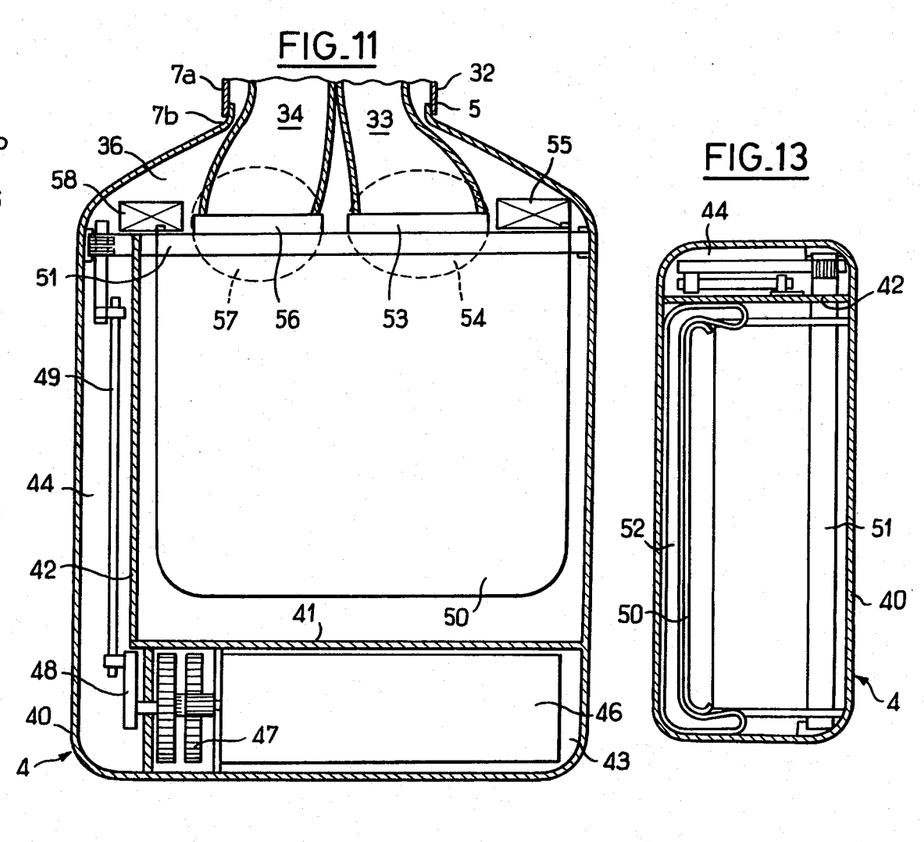
FIGS. 11, 12 and 13 show an example of embodiment of extra-pericardial unit for the total cardiac prothesis conforming with the present invention, respectively in front view, in left view and in view from above with torn-out parts.
Figure 12:
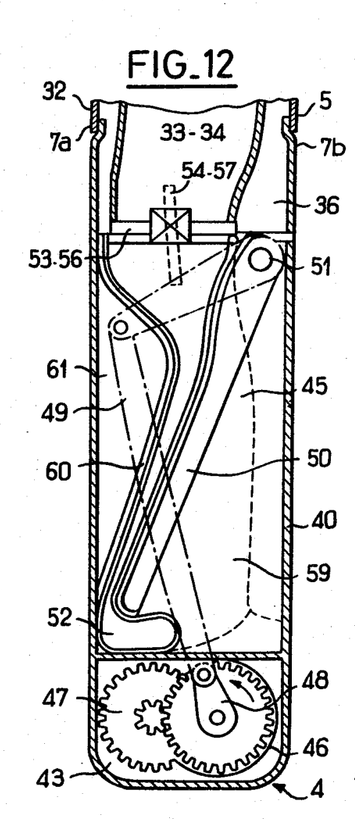

(2) The free inner space 36, as abovementioned and shown in FIGS. 11, 12 and 13, intercommunicates the dead spaces of pumping units 3 and 4. The latter operating in opposition, said inner free space 36 enables the gas volume, expelled by the pump from one of the units, to be displaced toward the other.

It thus acts as a volume compensation chamber, necessary for the operation of membrane pumps with a pushing plate. Moreover, it provides for the balancing of the variations in atmospheric pressure. This inner space thus solves with smartness the delicate problem of the compliance chamber, mentioned by many authors.

(3) The pump of the power extra-pericardial unit 4 is liable to produce hydraulic hammerings in pipe 33 extending the left auricle. However, this has no detrimental effect since, when such hydraulic hammerings occur, pipe 33, of very flexible consistency, radially expands, this expansion being made possible by the free space 36. Thus, pipe 33, in association with free space 36, acts as a blood reservoir in the same manner as an auricle: it may thus be considered as a complementary left auricle.

(4) Optionally, in order to enhance the function of free space 36, the envelope of the wall (which may be a part of the envelope 8) surrounding pipes 33 and 34, inside the pericardial unit 3, is flexible instead of being rigid.

An embodiment of the extra-pericardial pumping unit 4 is shown in FIGS. 11, 12 and 13. This embodiment comprises a casing 40, for example shaped as a flat parallelepiped, in two parts.

In casing 40, partitions 41, 42 define cavities 43, 44 and 45. In the lower cavity 43 are arranged an electric motor 46 and a reducer 47, connected, through a crank 48 and a rod 49 housed in the lateral cavity 44, to a pushing plate 50, arranged in the upper cavity 45. The pushing plate 50 may, upon actuation of motor 46, of reducer 47, of crank 48 and of rod 49, oscillate about an axis 51 transversal to the casing 40. The pushing plate 50 is suspended in inclined position from its axis 51.

In cavity 45 is housed a tight bag 52, tightly connected to an input and to an output orifices, provided with systems for quick coupling to electric-control valves.

The input orifice is provided with a quick coupling system 53 ensuring an easy connection with flexible pipe 33. A valve 54 (shown in dotted line in open position) is placed in said quick coupling system 53 and is controlled by an electro-magnet 55.

Similarly, the output orifice is provided with the quick coupling system 56 for an easy connection to the more rigid pipe 34. A valve 57 (also shown in dotted line, in open position) is arranged in said quick coupling system 56 and is controlled by electro-magnet 58.

Thanks to the quick coupling system 7a, 7b, the tubular envelope 32 of the connection line 5 may be connected to casing 40, the inner free space 36 of the connection line 5 being then in communication with the dead space 59, defined within cavity 45, externally to the tight bag 52, and on the side of the pushing plate 50 opposite thereto.

It can thus be seen that, thanks to the quick coupling systems 7a, 7b, 53 and 56, it is easy to connect unit 4 to line 5 or to disconnect it therefrom and hence to establish or cut off the connection between the two units 3 and 4.

FIG. 12 shows in solid line the extreme expelling position (through coupling ends 56 and pipe 34) of pump 50-52 and in dotted line the extreme aspiration position (through pipe 33 and coupling end 53) of said pump.

In a similar manner as for pumping unit 3, the membrane of bag 52 rolls on the pushing plate 50 and motor 46 and the electro-magnets 55 and 58 are controlled by micro-processor.

Of course, the remarks on the actuation system by pushing plate and the advantages of the rod-crank system, above-indicated, are the same for the extra-pericardial unit 4.

Inside cavity 45, on the side opposite to the pushing plate 50 with respect to the blood bag 52, a fixed wall 60 may be provided for decreasing the dead volume of the blood bag, so as to lighten the assembly and replace this incompressible dead volume by a dead volume 61 in communication for gases with spaces 59 and 36, thereby decreasing to the same extent the gas flow rate through space 36 of the connection line 5.

Figure 14:
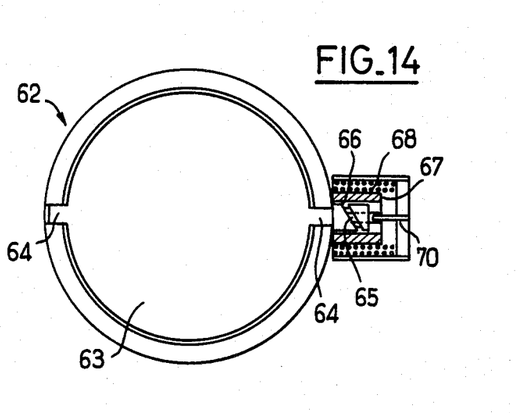
FIGS. 14 and 15 diagrammatically show, respectively in plane view with partial cross-section, and in side view, a first embodiment of the electric-control valve for the pericardial and extra-pericardial units of the total cardiac prothesis according to the invention.
Figure 15:
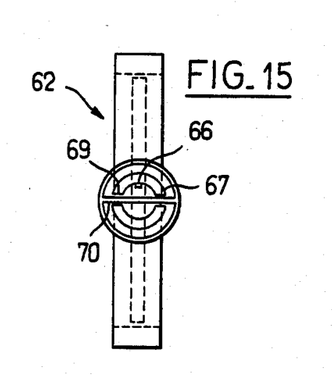

The electric-control valve 62, shown in FIGS. 14 and 15, (which can be used as valve 25, 26, 54 or 57) comprises a single circular disc 63 rotable about a diametral axis 64.

This axis 64 comprises a helical slot 65 wherein can slide a lug 66 integral with an iron core 67. The core 67 may axially slide in a solenoid 68 when the latter is fed with electric current. The core 67 cannot revolve about its axis, since it is provided with a slot 69 which slides on the small plate 70, integral with the solenoid frame, the axial displacement of said core 67 thus producing the rotation of disc 63.

Disc 63 might also be actuated by the provision of a permanent magnet (not shown) secured to axis 64 and placed at the center of a solenoid whose axis is perpendicular to axis 64. Thus, the passage of current through the solenoid results in such a positioning of the permanent magnet that its axis coincides with that of the solenoid, thus resulting in an action on the position of the valve. In an alternative embodiment, the axis 64 might be merely connected to the rotor of a rudimentary D.C. electric motor.

Figure 16:
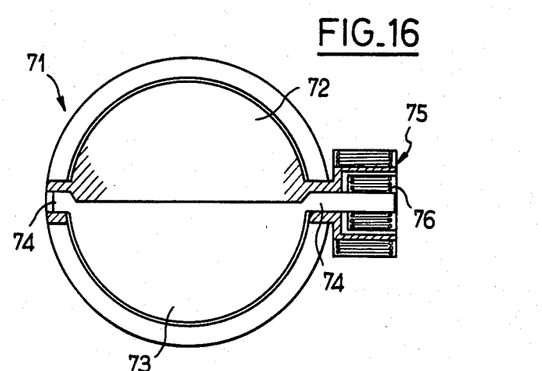
FIGS. 16 and 17 diagrammatically show, respectively in plane view with partial cross-section and in diametral cross-section, a second embodiment of the electric-control valve for the prothesis according to the invention.
Figure 17:
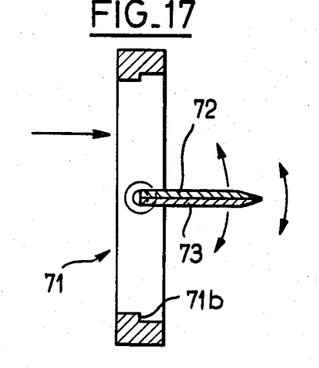

The embodiment of electric-control valve 71, shown in FIGS. 16 and 17, comprises two small semi-circular plates 72 and 73, rotable about the same geometrical axis 74.

Hence their privots 74 are concentric.

Plate 72 is connected (for its angular displacements) to the outer cage 75 of an electric motor.

Plate 73 is connected to the inner cage 76 of the same motor.

Consequently, the passage of electric current results in an angular displacement of plate 72 with respect to plate 73, although the electric motor has no external angular bearing.

Thus, in open position (shown in FIG. 17) the two semi-circular plates 72 and 73 are pressed against each other but may take together any angular position with respect to the axis of the fluid stream.

Accordingly, the fluid itself will give them their optimum position during the whole flowing period, this being an important factor for reducing the pressure drop through the valve. During the closure of the valve, the same is true and the contact of the plates 72 and 73 with the stop-member 71b generally does not occur at the same time.

Figure 18:
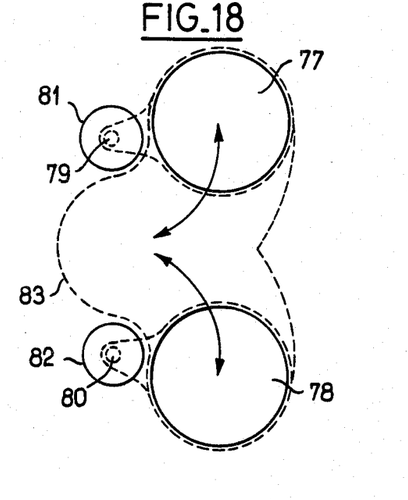
FIGS. 18 and 19 diagramatically illustrate, respectively a view from above and a side view of a third embodiment of double electric-control valve, more specially adapted to the extra-pericardial pumping unit of the total cardiac prothesis according to the invention.
Figure 19:
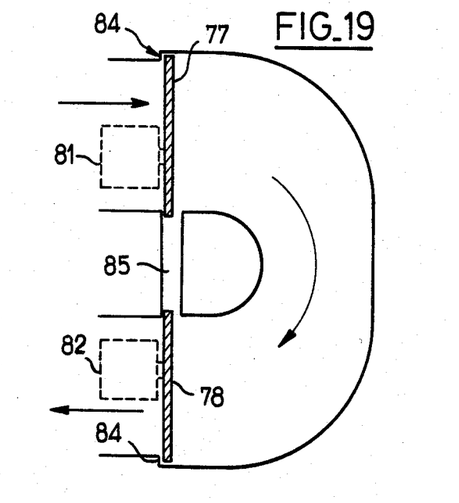

The third embodiment of valves, illustrated in FIGS. 18 and 19, is more particularly destined to the extrapericardial unit 4. As a matter of fact, its structure obliges to have two valves in the same plane. It offers the advantage of completely avoiding the pressure drops. This embodiment comprises two valves 77 and 78 respectively hinged on axes 79 and 80, perpendicular to the plane of the valves and parallel to the axis of the fluid streams.

Electric motors 81 and 82 or any other system, shift them in turn from their closure position to a location in a cavity 83, thus releasing completely the passage for the fluid streams.

The contact between valves 77 and 78 and the bearing members 84 is never complete in order to avoid any damage to the blood: in fact the strains are supported by axes 79 and 80.

It should be possible optionally to consider the use of a single motor and a single valve, to more or less completely obturate sequentially the two fluid streams.

Figure 20:
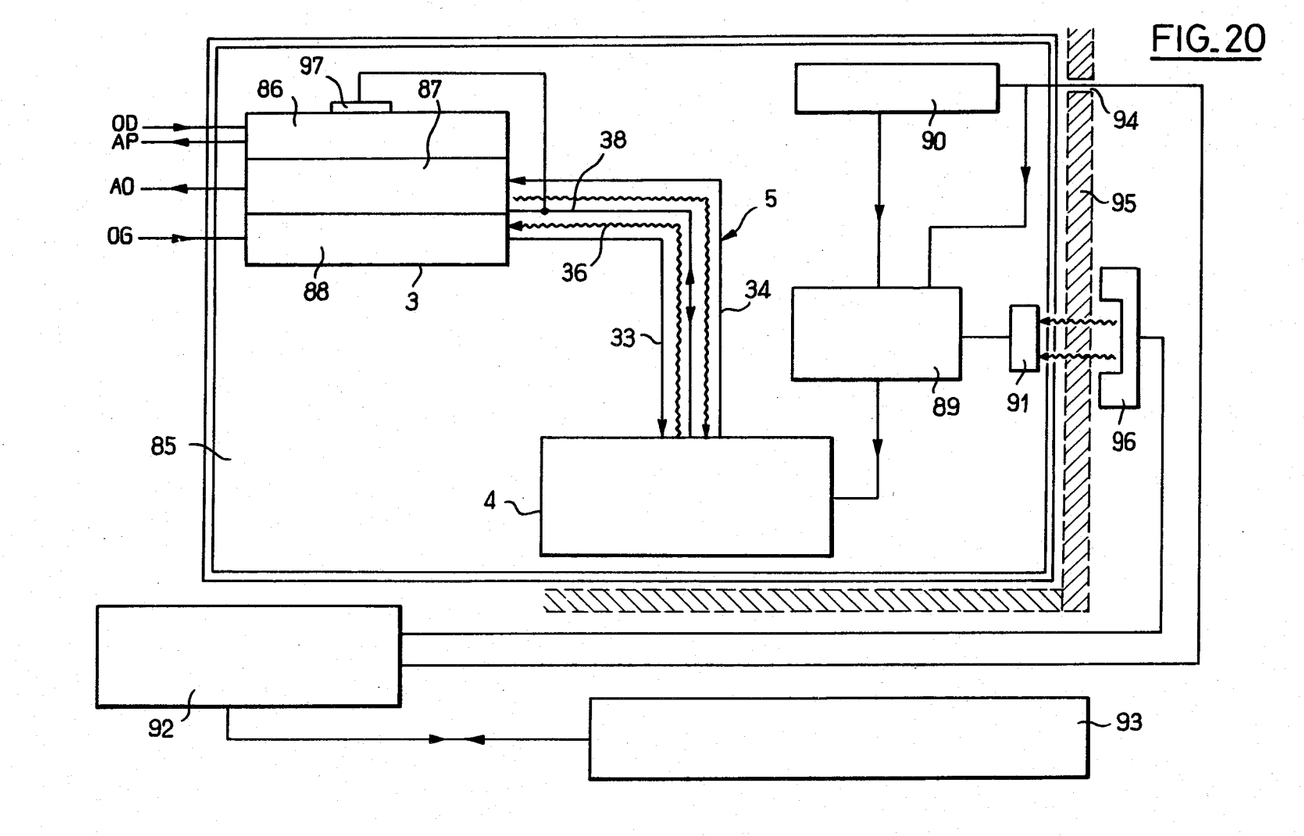
FIG. 20 gives a synoptic diagram of the prothesis of the invention.

FIG. 20 shows a synoptic diagram of the prothesis according to the invention. The assembly 85 of implanted elements comprises:

in the pericardial cavity, unit 3 which assumes the ventrical function 86 of passage between the right auricle RA and the pulmonary artery PA, the function 87 of artery connection between unit 4 and aorta AO and the coupling function 88 between the left auricle LA and unit 4;

the connection line 5 comprising pipe 33 which acts as a common pulmonary vein, extending the left auricle, pipe 34 acting as arterial duct connected to aorta, the space 36 acting as complementary left auricle and as volume compensation chamber or compliance chamber, and the electric connection 38;

in an extra-pericardial cavity, unit 4 acting as power left ventricle;

an electronic unit 89 used for regulations, control, etc . . .

implantable secondary batteries 90 and/or a high frequency receiver 91.

This assembly 85 of implanted elements may be connected to one or more portable external sub-assemblies 92 (electronics, rechargeable external batteries, etc . . . ) and to an external diagnosis and watching console 93, taking account of the circulatory parameters and of the prothesis parameters.

Between the implanted elements 85 and the assemblies 92 and 93, percutaneous connections may be provided by means of passage-ways 94 through the skin 95, and/or transcutanean connections, by means of a high frequency transmetting and receiving system 91, 96.

In FIG. 20, sensor 97 diagrammatically shown in the pericardial unit 3, is adpated to sense the venous return blood pressure and to monitor the rythm of the prothesis. For this purpose, sensor 97 is coupled to connector 38 passing through the connection line 5.

What is claimed is:

1. A total cardiac prothesis comprising two pumps, respectively representing the right heart and the left heart, as well as a control device of said pumps (89, 90, 92, 93), actuating said pumps in opposition, said prothesis also comprising an undissociable functional unit formed of:
   a pericardial unit (3) destined to be housed in the cavity (2) of the natural heart to be replaced (1) and enclosed in a tight envelope (8) provided with four coupling orifices (25, 26, 29 and 30), respectively adpated to be connected to the right auricle RA, to the pulmonary artery PA, to the left auricle LA, and to aorta AO, said orifices (25 and 26) for coupling the right auricle to the pulmonary artery PA being provided with valves used respectively as inlet orifice and outlet orifice of a first pump (13, 14) housed in said envelope (8) and destined to assume the right heart function of the natural heart to be replaced;
   an extra-pericardial unit (4), destined to be housed in a physiologically neutral space of the receiving sick person and to assume the function of the left heart of the natural heart to be replaced (1), said extra-pericardial unit comprising a second pump (50, 52) enclosed in a tight envelope (40) provided with an inlet orifice (53) and an outlet orifice (56), each provided with a valve;
   a functional connection line (5) between said units, comprising:
      a first duct (33) passing through said envelope (8) of said pericardial unit (3) and connecting the orifice (29) of the latter corresponding to the left auricle LA with the inlet orifice (53) of the second pump (50,52) incorporated into said extra-pericardial unit (4),
      a second duct (34) passing through said envelope (8) of said extra-pericardial unit (3) and connecting the orifice (30) thereof corresponding to aorta AO with the outlet orifice (56) of the second pump (50, 52) incorporated into said extra-pericardial unit (4),
      a third duct (32) establishing communication for the gases between the sides of said first and second pumps opposite to the blood flow therethrough.

2. A total cardiac prothesis according to claim 1, wherein said pericardial unit (3) comprises an electromechanical system (19, 20, 21, 22) for actuating said first pump (13, 14).

3. A total cardiac prothesis according to claim 1 or 2, wherein said envelope (8) of said pericardial unit (3)

has, at least approximately, the shape, the volume and the weight of the natural heart to be replaced, and the locations on said envelope (8) of orifices (25, 26, 29, 30) for respective couplings with the right auricle RA, the pulmonary artery PA, the left auricle LA and aorta AO, correspond at least substantially, to the natural disposition of these auricles and arteries.

4. A total cardiac prothesis according to any one of claims 1 to 3, wherein a sensor (97) is placed in said pericardial unit (3) for sensing the pressure of the venous blood at the input of said first pump (13, 14) and for regulating the operation of the prothesis in response to the measured blood pressure.

5. A total cardiac prothesis according to any one of claims 1 to 4, wherein in said pericardial unit (3), the valves provides in orifices (25, 26) for coupling with the right auricle and the pulmonary artery are of the electric-control type.

6. A total cardiac prothesis according to any one of claims 1 to 5, wherein said first pump (13, 14) is of the membrane type and the electro-mechanical actuating system comprises a pushing plate (14) in direct contact with said membrane.

7. A total cardiac prothesis according to any one of claims 4 to 6, wherein said sensor (97) is mounted on membrane (13) of said first pump (13, 14).

8. A total cardiac prothesis according to any one of claims 1 to 7, wherein said connection line (5) connects the lower part of said envelope (8) of said pericardial unit (3) to the upper part of the envelope (40) of said extra-pericardial unit (4).

9. A total cardiac prothesis according to any one of claims 1 to 8, wherein said pericardial unit (3) and said connection line (5) are rigidly secured to each other, whereas detachable junction couplings (7a, 7b, 53, 36) are provided to connect the first, second and third ducts (33, 34, 32) of said connection line with said extra-pericardial unit (4).

10. A total cardiac prothesis according to any one of claims 1 to 5, wherein said third duct (32) of said connection line (5) is longitudinally flexible but radially rigid and contains said first and second ducts (33 and 34).

11. A total cardiac prothesis according to any one of claims 2 to 5, wherein an electric cable (38), housed in said third duct (32), interconnects said pericardial (3) and extra-pericardial (4) units.

12. A total cardiac prothesis according to any one of claims 1 to 11, wherein said second pump (50, 52) is of the membrane type and the extra-pericardial unit (4) comprises an electro-mechanical system (46, 47, 48, 49) with a pushing plate (50) for actuating said second pump.

13. A total cardiac prothesis according to any one of claims 1 to 12, wherein each of the two valves (54, 57) incorporated to said extra-pericardial unit (4) is of the type with electrically controlled opening and closing.

14. A total cardiac prothesis according to one of claims 2, 5, 11, 12 and 13, wherein the control device (89, 90, 92, 93) comprises a micro-processor controlling the electro-mechanical systems of said first and second pumps, as well as the electric-control valves of said pericardial and extra-pericardial units.

15. A total cardiac prothesis according to claim 14, wherein the control of the electro-mechanical system and of the valves of said pericardial unit (3) passes through said extra-pericardial unit (4) and the electric cable (38) is housed in said third duct (32) of said connection line (5).

16. A total cardiac prothesis according to claim 6 or 12, wherein said electro-mechanical system comprises an electric motor (19 or 46) and a rod-crank system (21, 22 or 48, 49) avoiding the reversion of the revolving direction of said electric motor.

17. A total cardiac prothesis according to claim 16, wherein the relative location of the articulations of the pushing-plate, of the rod and of the crank is so determined that the forward and backward velocities of the pushing-plate are adapted to the physiological requirements and do not require but a small cyclic adaptation of the motor running speed.

18. A total cardiac prothesis according to claim 6, wherein the pericardial unit (3) is of elongate shape and the pushing-plate (14) is articulated about a line approximatively coinciding with the length of said pericardial unit (3), in order to give it the larger possible surface.

19. A total cardiac prothesis according to claim 18, wherein said pushing-plate (14) is curved.

20. A total cardiac prothesis according to any one of claims 5 to 13, wherein said electric-control valves are of the type with two semi-circular clappers (72, 73) hindged about a common diametral axis (74) so as to be able to take any position between an extreme position wherein said clappers are in the same plane and opposite and an other extreme position wherein said clappers are joined back to back.

* * * * *